United States Patent
Dhal et al.

(10) Patent No.: US 6,271,264 B1
(45) Date of Patent: *Aug. 7, 2001

(54) POLYMERS CONTAINING SPIROBICYCLIC AMMONIUM MOIETIES AS BILE ACID SEQUESTRANTS

(75) Inventors: Pradeep K. Dhal, Acton; Steven C. Polomoscanik, Lexington, both of MA (US)

(73) Assignee: GelTex Pharmaceuticals, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/203,319

(22) Filed: Dec. 1, 1998

(51) Int. Cl.$^7$ .................. A61K 31/14; A61K 31/045; A61K 31/13; A61K 31/33; A61K 31/74

(52) U.S. Cl. ................ 514/642; 424/78.01; 424/78.08; 424/78.36; 424/78.37; 424/78.38; 514/183; 514/210.16; 514/212.02; 514/214.01; 514/222.8; 514/230.5; 514/249; 514/278; 514/279; 514/409; 514/410; 514/411; 514/412; 514/413; 514/434; 514/456; 514/459; 514/646; 514/660; 514/661; 514/662; 514/727; 514/729; 514/740; 514/741

(58) Field of Search .................. 514/183, 210–215, 514/217, 222.2, 224.2, 228.2, 229.5, 230.5, 247, 248, 256–259, 277–279, 306, 307, 315–324, 326, 332–334, 336–340, 342, 408–412, 430, 432–434, 444, 449, 451, 453, 459, 579, 642, 772.1, 772.3, 772.7, 836, 210.16, 212.02, 214.01, 222.8, 249, 278, 646, 660, 661, 662, 727, 729, 740, 741; 424/78.01, 78.08, 78.1, 78.11, 78.12, 78.13, 78.14, 78.15, 78.17, 78.19, 78.22, 78.23, 78.36, 78.37, 78.38, DIG. 6

(56) References Cited

U.S. PATENT DOCUMENTS

| | | | |
|---|---|---|---|
| 3,288,770 | 11/1966 | Butler | 260/88.3 |
| 4,046,766 | 9/1977 | Costin | 260/290 |
| 4,360,434 | 11/1982 | Kawaguchi et al. | 210/500.2 |
| 4,812,540 | 3/1989 | Kageno et al. | 526/218.1 |
| 5,185,411 | 2/1993 | Jueptner et al. | 526/200 |
| 5,393,338 | * 2/1995 | Pudney et al. | 106/238 |
| 5,496,545 | 3/1996 | Holmes-Farley et al. | 424/78.11 |
| 5,556,619 | * 9/1996 | Royce et al. | 424/78.08 |
| 5,607,669 | 3/1997 | Mandeville, III et al. | 424/78.12 |
| 5,618,530 | 4/1997 | Mandeville, III et al. | 424/78.12 |
| 5,624,963 | 4/1997 | Mandeville, III et al. | 514/789 |
| 5,667,775 | 9/1997 | Holmes-Farley et al. | 424/78.11 |
| 5,679,717 | 10/1997 | Mandeville, III et al. | 514/742 |
| 5,693,675 | 12/1997 | Mandeville, III et al. | 514/742 |
| 5,703,188 | 12/1997 | Mandeville, III et al. | 526/290 |

FOREIGN PATENT DOCUMENTS

| | | |
|---|---|---|
| 42 00 139 A1 | 7/1993 | (DE) . |
| 0 142 962 A2 | 5/1985 | (EP) . |
| 0 280 445 A1 | 8/1988 | (EP) . |
| WO 95/34585 | 12/1995 | (WO) . |
| WO 96/39449 | 12/1996 | (WO) . |
| WO 98/29107 A2 | 7/1998 | (WO) . |

OTHER PUBLICATIONS

U.S. Patent application No. 08/964,498, "Poly(Diallylamine)–Based Phosphate Binders" filed on Nov. 5, 1997, by W. Harry Mandeville, III and Stephen Randall Holmes–Farley.

McLean, C.D. et al., "Cyclopolymerization. VI. Preparation and Properties of Crosslinked Polyamines by Cyclopolymerization," *J. of Macromol. Sci.–Chem.*, A10 (5):857–873 (1976).

Negi, Youji et al., "Cyclopolymerization of Diallylamine Derviatives in Dimethyl Sulfoxide," *J. of Polymer Science*: Part A–1, 5:1951–1965 (1967).

Harada, Susume and Kunio Arai, "The Cyclo–copolymerization of Diallyl Compounds and Sulfur Dioxide, II: Diallyldimethylammonium Chloride and Sulfur Dioxide," *Die Makromolekulare Chem.* 107:64–77 (1967).

Harada, Susume and Kunio Arai, "The Cyclo–copolymerization of Diallyl Compounds and Sulfur Dioxide, III: Some Diallylamine Derivatives and Sulfur Dioxide," *Die Makromolekulare Chem.* 107:78–93 (1967).

Mathias, L.J., "Synthesis Cyclopolymerization and Copolymerization of 4–(Diallylamino)Pyridine: A New Polymer," *Polymer Reprints*, 26(1):182–183 (1985).

De Vynck, V., "Synthesis and Polymerization of N, N–Diallylpyrrolidinium Bromide," *Macromol. Rapid Commun.*, 18(8):149–156 (1997).

* cited by examiner

*Primary Examiner*—Jose' G. Dees
*Assistant Examiner*—Frank Choi
(74) *Attorney, Agent, or Firm*—Hamilton, Brook, Smith & Reynolds, P.C.

(57) ABSTRACT

The present invention relates to a method for sequestering bile acids in a patient and to particular polymers for use in the method. The method comprises administering a therapeutically effective amount of a spirobicyclic ammonium moiety-containing polymer composition to a mammal, such as a human, whereby bile acids are sequestered. The polymers of the invention comprise spirobicyclic ammonium moieties and optionally, further comprise a hydrophobic substituent, a quaternary ammonium-containing substituent or a combination thereof.

22 Claims, No Drawings

POLYMERS CONTAINING SPIROBICYCLIC AMMONIUM MOIETIES AS BILE ACID SEQUESTRANTS

BACKGROUND OF THE INVENTION

Biologically, cholesterol is eliminated from the body by conversion into bile acids and excretion as neutral steroids. Bile acids are synthesized from cholesterol in the liver and enter the bile as glycine and taurine conjugates. They are released in salt form in bile during digestion and act as detergents to solubilize and consequently aid in the digestion of dietary fats. Following digestion, bile acid salts are mostly reabsorbed by active transport in the ileum, complexed with proteins, and returned to the liver through hepatic portal veins. The small amount of bile acid salts not reabsorbed in the ileum is excreted via the distal ileum and large intestine, as a portion of the fecal material.

Therefore, reabsorption of bile acids, which can be present as the corresponding salts or conjugates, from the intestine conserves lipoprotein cholesterol in the bloodstream. As such, reducing reabsorption of bile acids within the intestinal tract can lower levels of bile acids circulating in the enterohepatic system thereby promoting replacement of bile acids through de novo synthesis from cholesterol, in the liver. The result is a lowering of circulating blood cholesterol levels.

One method of reducing the quantity of bile acids that are reabsorbed is the oral administration of compounds that sequester the bile acids within the intestinal tract and cannot themselves be absorbed. The sequestered bile acids consequently are excreted.

A need exists for sequestrants that bind bile acid salts and conjugates.

SUMMARY OF THE INVENTION

The invention relates to polymers comprising a spirobicyclic ammonium moiety-containing repeat unit, and to a method of using the polymers for sequestering bile acids in a patient.

In one aspect, the polymer comprises spirobicyclic ammonium-moiety containing repeat units represented by Structural Formulas (I) and (II), copolymers and salts thereof.

In one embodiment, the spirobicyclic ammonium moiety-containing polymers further comprise one or more additional monomers wherein the additional monomer is non-spirobicyclic. In another embodiment, the additional monomer is a multifunctional crosslinking co-monomer. In another embodiment the additional monomer is a nitrogen-containing monomer. In specific embodiments, the nitrogen-containing monomer comprises an amine, wherein one or more substituents are bonded to available amino nitrogen atoms of the polymer. Amino nitrogen atoms which are available for substitution include the nitrogen atoms of primary, secondary, and tertiary amines. Suitable substituents can include hydrophobic and/or quaternary ammonium-containing groups.

In a preferred aspect, the copolymers of the invention are crosslinked. In one embodiment, crosslinking is achieved through a multifunctional crosslinking co-monomer which is incorporated into two or more polymer chains. In another embodiment, crosslinking is achieved by means of a multifunctional crosslinking agent.

The method of the invention comprises orally administering to a mammal a therapeutically effective amount of a polymer comprising a spirobicyclic ammonium moiety-containing repeat unit, whereby, bile acids are sequestered and consequently excreted. The method of the invention is useful to reduce the levels of circulating cholesterol, to treat atherosclerosis and/or to treat hypercholesterolemia.

The spirobicyclic ammonium moiety-containing polymers provide many advantages over certain known bile acid sequestrants having a non-spirobicyclic quaternary ammonium group. Quaternary ammonium compounds can undergo degradation by, for example, Hofmann elimination. This type of degradation involves the cleavage of at least one of the four bonds involving the ammonium nitrogen atom thereby producing a double bond and a tertiary amine. As such, Hofmann elimination can result in the elimination of, for example, the trialkylamine from an alkyl trialkylammonium moiety, possibly diminishing the effectiveness of a bile acid sequestrant that comprises alkyl trialkylammonium moieties. In addition, the elimination products can, in some instances, cause undesirable side effects.

However, the spirobicyclic ammonium moieties of the invention have a structure which overcomes the disadvantages associated with Hofmann elimination. Namely, even though the spirobicyclic ammonium groups of the invention can still undergo cleavage of a bond between a carbon atom and the ammonium nitrogen atom, all of the carbon atoms which are bonded to the quaternary nitrogen atom are part of the spirobicyclic junction. Thus, tertiary amines and undesirable elimination products are not released from the polymers of the invention as a result of Hofmann elimination.

Additionally, the spirobicyclic ring structure of the polymers of the invention can provide improved structural matching with the steroidal skeleton of bile acids.

DETAILED DESCRIPTION OF THE INVENTION

The present invention relates to polymers and to methods of using the polymers for removing bile acids from a patient. The polymers of the invention comprise a spirobicyclic ammonium moiety-containing repeat unit and physiologically acceptable salts thereof.

The term "spirobicyclic" refers to a ring system comprising two rings which share a common atom. The shared atom can be referred to as the spiro atom or the spiro center. In the case of the spirobicyclic ammonium moiety-containing polymers of the invention the spiro atom is a nitrogen atom.

In one aspect the spirobicylic ammonium moiety-containing polymers can comprise, for example, a diallylamine repeat unit wherein the amino nitrogen atom is quaternized to form the spiro center of the spirobicylic ammonium moiety-containing polymer of the invention.

In this aspect, the polymer can comprise a repeat unit represented by Structural Formula (I) and/or (II).

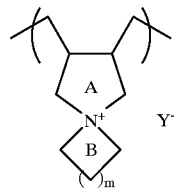

(I)

(II)

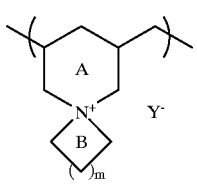

The rings labeled "A" and "B" are referred to herein as Ring A and Ring B. Ring A can be a five or six membered ring, and can be formed by the polymerization of diallylamine or certain diallylamine derivatives.

m can be an integer, such as an integer from zero to about seven.

Y is a negatively charged counterion.

Ring A and Ring B can each, independently, be unsubstituted or can have one or more substituents as described herein.

In particular embodiments, Ring B can contain one or more units of unsaturatiori and/or one or more additional heteroatoms such as oxygen, nitrogen and sulfur. For example, Ring B can be selected from Structural Formulas (III–XI).

(III)

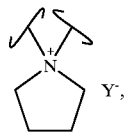

(IV)

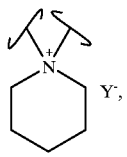

(V)

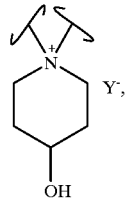

(VI)

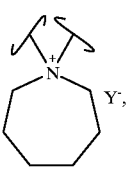

(VII)

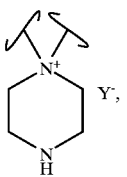

(VIII)

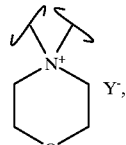

(IX)

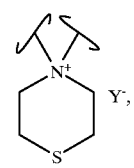

(X)

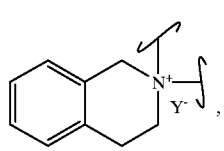

(XI)

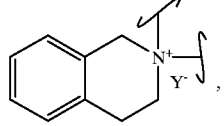

The symbol "∫" is used to indicate the bond between the spiro nitrogen atom and a carbon atom of Ring A. Thus, the nitrogen atom of Ring B that is bonded to two "∫", is the spiro atom that is shared by Ring A and Ring B.

Polymers comprising a repeat unit represented by Structural Formula (I) and/or (II), can be prepared by polymerization of suitable quaternary ammonium-containing diallylamine derivatives, which are also referred to herein as spirobicyclic ammonium-moiety containing monomers. For example, N,N-diallylpyrrolidinium bromide, N,N-diallylpiperidinium bromide, N,N-diallylhomopiperidinium bromide, N,N-diallyl(4-hydroxy)piperidinium bromide, N,N-diallyl 1,2,3,4-tetrahydroisoquinolinium bromide, N,N-diallyldecahydroquinolinium bromide and the like, which can be prepared by reacting a nitrogen-containing heterocycle with allyl bromide as described herein. Other pharmaceutically acceptable salts of diallylamine derivatives (e.g., N,N-diallylpyrrolidinium chloride, N,N-diallylpyrrolidinium acetate, N,N-diallylpyrrolidinium bicarbonate and the like) can also be used to prepare polymers comprising a repeat unit represented by Structural Formula (I) and/or (II).

Polymerization can be accomplished using techniques known in the art of polymer synthesis. (See, for example, Shalaby et al., ed., *Water-Soluble Polymers*, American Chemical Society, Washington, D.C. [1991]). The appropriate monomers can be polymerized by methods known in the art, for example, via a free radical addition process. In this case, the polymerization mixture includes a free-radical initiator. Suitable free-radical initiators include azobis (isobutyronitrile), azobis(4-cyanovaleric acid), 2,2'-azobis (2-amidinopropane)dihydrochloride, potassium persulfate, ammonium persulfate, and potassium hydrogen persulfate. Other suitable initiators include ionizing radiation and ultraviolet light. The free radical initiator is preferably present in the reaction mixture in an amount ranging from about 0.01 mole percent to about 5 mole percent relative to the monomer.

The polymers comprising a repeat unit represented by Structural Formulas (I) arid/or (II) can be obtained as homopolymers or as copolymers which can further comprise one or more additional monomers, for example, allyl alcohol, vinyl alcohol, ethylene oxide, propylene oxide, substituted and unsubstituted acrylates and methacrylates, such as hydroxyethylacrylate, hydroxyethylmethacrylate, hydroxypropylacrylate, hydroxypropylmethacrylate, polypropylene glycol) monomethacrylate, poly(ethylene glycol) monomethacrylate, acrylic acid, carbon monoxide, and sulfur dioxide. In copolymers comprising sulfur dioxide, the polymer backbone includes —$SO_2$— units between pairs of spirobicyclic ammonium moiety-containing monomers or repeat units.

Copolymers can also further comprise a multifunctional crosslinking co-monomer, for example, diacrylates, triacrylates, tetraacrylates, dimethacrylates, diacrylamides, diallylacrylamides and dimethacrylamides. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis (methacrylamide), ethylidene bis(acrylamide), ethylidene bis(methacrylamide), pentaerythritol tetraacrylate, trimethylolpropane triacrylate, bisphenol A dimethacrylate, bisphenol A diacrylate, 1,2-ethylene-bisacrylamide and 1,6-bis (diallylmethylammornium chloride)hexane. Other suitable multifunctional crosslinking co-monomers include polyvinylarenes, such as dtivinylbenzene.

Copolymers can also further comprise a nitrogen containing monomer, wherein the nitrogen atom is not a spiro center. Suitable n:Ltrogen-containing monomers include, for example, amine-containing and ammonium-containing monomers.

The term "amine-containing monomer", as used herein, includes any monomer or repeat unit characterized by an amino nitrogen atom. Thus, amine-containing co-monomers include monomers which have been chemically altered through chemical reactions such as hydrolysis, nucleophilic substitution and reduction to yield a repeat unit characterized by an amino nitrogen atom, as well as monomers which contain an amino nitrogen or polymers which can be altered by said chemical reactions to yield a product that contains a repeat unit which contains an amino nitrogen atom. Suitable amine-containing monomers include, but are not limited to, for example, allylamine, diallylamine, diallyl methylamine, vinylamine, aminoalkyl(meth)acrylates and vinylimidazole.

The term "ammonium-containing monomer", as used herein, refers to a monomer which comprises an ammonium nitrogen atom which is not a spiro center, and includes monomers which have been chemically altered through chemical reactions such as hydrolysis, nucleophilic substitution and reduction to yield a repeat unit characterized by an ammonium nitrogen atom, as well as monomers which contain an ammonium nitrogen or polymers which can be altered by said chemical reactions to yield a product that contains a repeat unit which contains an ammonium nitrogen atom. An ammonium-containing monomer can be associated with a negatively charged counterion as described herein. Ammonium-containing monomers include, for example, vinylbenzyl trimethyl ammonium chloride, diallyl dimethyl ammonium chloride, diallyl di(beta-hydroxy ethyl) ammonium chloride, diallyl di(beta-ethoxy ethyl) ammonium chloride, diallyl ammonium chloride and the like.

Preferably, the ammonium-containing monomer is represented by Structural Formula (XII) and/or (XIII):

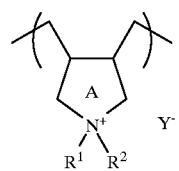

(XII)

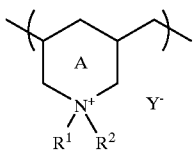

(XIII)

$R^1$ and $R^2$ can each independently be hydrogen, a $C_1$–$C_{30}$ aliphatic group, $C_1$–$C_{30}$ alkyl group, a quaternary ammonium-containing group or an aromatic group.

Copolymers of the invention can be formed by the methods described above, for example, a heterocyclic diallylamine derivative (e.g., N,N-diallylpyrrolidinium bromide, N,N-diallylpiperidinium bromide, N,N-diallylhomopiperidinium bromide, N,N-diallyl(4-hydroxy)piperidinium bromide, N,N-diallyl 1,2,3,4-tetrahydroisoquinolinium bromide, N,N-diallyldecahydroquinolinium bromide) can be polymerized with one or more additional monomers (e.g., a nitrogen-containing monomer). The quantity of spirobicyclic ammonium moieties present in a copolymer of the invention can be controlled by altering the relative amounts of spirobicyclic ammonium moiety containing monomer and co-monomer which are copolymerized. The copolymers of the invention contain about 25% to about 99.5% spirobicyclic ammonium moiety-containing monomer by weight, based upon the combined weight of spirobicyclic ammonium moiety-containing monomer and co-monomer. In a preferred embodiment, the copolymers contain at least about 50% to about 99.5% spirobicyclic ammonium moiety-containing monomer by weight, based upon the combined weight of spirobicyclic ammonium moiety-containing monomer and co-monomer.

In a preferred embodiment, the additional monomer comprising the copolymer is an amine-containing monomer.

Copolymer compositions which comprises a repeat unit represented by Structural Formula (I) and/or (II) and an amine-containing monomer can further comprise substituents which are bonded to available amino nitrogen atoms of the copolymer. Amino nitrogen atoms which are available for substitution include the nitrogen atoms of primary, secondary and tertiary amines. These substituents can include a hydrophobic group such as a normal or branched alkyl group of at least about four carbon atoms, a quaternary ammonium-containing group such as an alkyltrialkyl ammonium group or a combination thereof. It is to be understood that one or more substituents can be bonded to the same or different nitrogen atoms of the copolymer.

A "hydrophobic group", as the term is used herein, is a chemical group which, as a separate entity, is more soluble in octanol than water. For example, the octyl group ($C_8H_{17}$) is hydrophobic because its parent alkane, octane, has greater solubility in octanol than in water. The hydrophobic group can be a saturated or unsaturated, substituted or unsubstituted hydrocarbon group. Such groups include substituted and unsubstituted, normal, branched or cyclic alkyl groups having at least about four, preferably at least about six, carbon atoms, substituted or unsubstituted arylalkyl or heteroarylalkyl groups and substituted or unsubstituted aryl or heteroaryl groups. Preferably the hydrophobic group includes an alkyl group of between about six and twenty-four carbon atoms. More preferably the hydrophobic group includes an alkyl group of between six and about fourteen carbon atoms. Suitable hydrophobic groups include, for example, n-hexyl, n-heptyl, n-octyl, n-nonyl, n-decyl, n-undecyl, n-dodecyl, n-tridecyl, n-tetradecyl, n-hexadecyl, n-octadecyl, n-eicosyl and combinations thereof. Other examples of hydrophobic groups include haloalkyl groups of at least about four, preferably at least about six, carbon atoms (e.g., 10-halodecyl), hydroxyalkyl groups of at least about four, preferably at least about six, carbon atoms (e.g., 11-hydroxyundecyl), and aralkyl groups (e.g., benzyl).

As used herein, aliphatic groups include straight chained, branched or cyclic $C_1$–$C_{24}$ hydrocarbons which are completely saturated or which contain one or more units of unsaturation. For example, suitable aliphatic groups include substituted or unsubstituted linear, branched or cyclic $C_1$–$C_{24}$ alkyl, alkenyl or alkynyl groups. Optionally, one or more of the carbon atoms in an aliphatic group can be replaced by a heteroatom such as oxygen, nitrogen or sulfur.

An "alkyl group" is a saturated aliphatic group, as defined above.

Acyl groups include substituted and unsubstituted aliphatic carbonyl, aromatic carbonyl, aliphatic sulfonyl and aromatic sulfonyl.

Aromatic groups include carbocyclic aromatic rings (e.g. benzyl, phenyl, etc.) and fused polycyclic aromatic ring systems (e.g. naphthyl, anthracyl, etc.). In addition, aromatic groups include heteroaryl rings (e.g. pyridine, thiophene, furan, etc.) and polycyclic aromatic ring systems in which a carbocyclic aromatic ring or heteroaryl ring is fused to one or more other rings. For example, 2-benzothienyl, 3-benzothienyl, 2-benzofuranyl, 3-benzofuranyl, 2-indolyl, 3-indolyl, 2-quinolinyl, 3-quinolinyl, 2-benzothiaz[]ole, 2-benzooxazole, 2-benzimidazole, 2-quinolinyl, 3-quinolinyl, 1-isoquinolinyl, 3-quinolinyl, 1-isoindolyl, 3-isoindolyl, and acridinyl.

As used herein, the term "heterocyclic ring" or "heterocycle" refers to carbocyclic or cycloalkyl ring in which one or more of the carbon atoms is replaced by a heteroatom such as oxygen, nitrogen or sulfur. For example, aziridine, azedine, pyrrolidine, piperidine, piperazine, morpholine, thiazine, tetrahydrofuran, tetrahydropyran, tetrahydrothiophene, tetrahydrothiopyran and the like.

Ring A, Ring B, a heterocyclic ring, a carbocyclic ring, an alkyl group, an aliphatic group and an aromatic group can be substituted. Suitable substituents for these rings and groups can include, for example, —OH, an electron withdrawing group, a halogen (—Br, —Cl, —I and —F), —O(aliphatic, substituted aliphatic, benzyl, substituted benzyl, aromatic or substituted aromatic group), —CN, —NO$_2$, —COOH, —NH$_2$, —NH(aliphatic group, substituted aliphatic, benzyl, substituted benzyl, aromatic or substituted aromatic group), —N(aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —CONH$_2$, —CONH(aliphatic, substituted aliphatic group, benzyl, substituted benzyl, aromatic or substituted aromatic group), —CON(aliphatic, substituted aliphatic group, benzyl, substituted benzyl, aromatic or substituted aromatic group)$_2$, —SH, —So$_k$(aliphatic, substituted aliphatic, benzyl, substituted benzyl, aromatic or substituted aromatic group) (k is 0, 1 or 2), —NH—C(=NH)—NH$_2$ and —C(=NH)—NH$_2$. A substituted non-aromatic heterocyclic ring, benzyl group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic group or a substituted aromatic group can have more than one substituent. When Ring B, a heterocyclic ring, a carbocyclic ring or an aromatic ring is substituted by one or more additional rings, the rings can be fused.

Suitable quaternary ammonium-containing groups include alkyl trialkylammoniums also referred to as ammonioalkyl groups. The term, "ammornioalkyl", as used herein, refers to an alkyl group which is substituted by a nitrogen bearing three additional substituents. Thus, the nitrogen atom is an ammonium nitrogen atom which bears an alkylene substituent, which links the ammonium nitrogen atom to the nitrogen atom of the amine-containing copolymer, and three additional terminal alkyl substituents having from about one to twenty-four carbon atoms. A "terminal substituent" of the quaternary ammonium, as the term is employed herein, is any one of the three substituents on the quaternary ammonium nitrogen which is not the carbon chain linking the amino nitrogen atom of the copolymer and the nitrogen atom of the quaternary ammonium center.

An ammonioalkyl group will further include a negatively charged counterion, such as a conjugate base of a pharmaceutically acceptable acid. Suitable counterions include, for example, Cl$^-$, Br$^-$, CH$_3$SO$_3^-$, HSO$_4^-$, SO$_4^{2-}$, HCO$_3^-$, CO$_3^{2-}$, acetate, citrate, lactate, succinate, propionate, butyrate, ascorbate, maleate, folate, an amino acid derivative and a nucleotide.

Preferred ammonioalkyl groups can have the general formula:

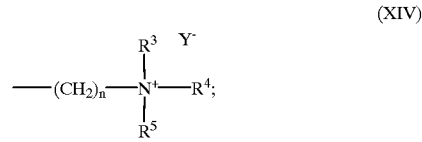

(XIV)

wherein R$^3$, R$^4$ and R$^5$ independently can be a normal or branched, substituted or unsubstituted alkyl group having about one to twenty-four carbon atoms;

n is an integer, for example, n can be from three to about twenty; and,

Y is a negatively charged counterion.

The alkyl group which provides the alkylene linking group between the amino nitrogen atom of the amine-containing polymer and the ammonium nitrogen of the alkyl trialkylammonium group can be three to about twenty carbon atoms in length. Examples of preferred alkylene linking groups are propylene, butylene, pentylene, hexylene, octylene and decylene groups. Examples of suitable quaternary ammonium-containing groups include, but are not limited to:

3-(trimethylammonio)propyl;
4-(trimethylammonio)butyl;
5-(trimethylammonio)pentyl;
6-(trimethylammonio)hexyl;
8-(trimethylammonio)octyl;
10-(trimethylammonio)decyl;
12-(trimethylammonio)dodecyl and combinations thereof. A preferred quaternary ammonium-containing group is a 6-(trimethylammonio)hexyl group.

Alternatively, a quaternary ammonium-containing group comprises one or more substituents (i.e., either a terminal substituent or the alkylene linking group and combinations thereof) which are hydrophobic as defined hereinabove. For example, the ammonium nitrogen atom of the quaternary ammonium-containing group is bonded to the amino nitrogen atom of the polymer by an alkylene linking group having 4, preferably 6, or more carbon atoms. In a particular embodiment, the quaternary ammonium-containing group is represented by Structural Formula (XIV) wherein $R^3$ and $R^4$ are dodecyl groups, $R^5$ is a methyl group, n is 3 and Y is $Br^-$.

Particular examples of quaternary ammonium-containing groups containing hydrophobic substituents include, for example:
4-(dioctylmethylammonio)bbutyl;
3-(dodecyldimethylammonio)propyl;
3-(octyldimethylammonio)propyl;
3-(decyldimethylammonio)p:ropyl;
6-(dimethyldecylammonio)hexyl;
6-(decyldimethylammonio)hexyl;
3-(tridecylammonio)propyl;
3-(docosyldimethylammonio)propyl;
6-(docosyldimethylammonio)hexyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonic)hexyl;
4-(heptyldimethylammonio)butyl;
4-(dioctylmethylammonio)hbutyl;
6-(octyldimethylammonio) hexyl;
12-(decyldimethylammonio)dodecyl;
3-(dimethylundecylammmnio)propyl; and
3-(tetradecyldimethylammonio)propyl.

Substitution of the amine-containing copolymers of the invention with a hydrophobic group, a quaternary ammonium-containing group, or a combination thereof can be achieved by reaction of the copolymer with an alkylating agent to yield an alkylated copolymer. Alternatively, an amine-containing monomer can be alkylated and the alkylated monomer can be copolymerized with a monomer represented by Structural Formula (I), (II) or a combination thereof.

An "alkylating agent," as that term is employed herein, refers to a reactant that, when reacted with an amine-containing monomer or a polymer characterized by an amine-containing repeat unit, results in the covalent bonding of a substituent (e.g., a hydrophobic group or quaternary ammonium-containing group as described herein) to one or more of the aminao nitrogen atoms of the monomer or polymer. It is to be understood that under certain conditions, hydroxyl groups contained in the polymer compositions can also react with alkylating agents. Further, when multiple substituents are employed, they can be bonded to the same and/or different amino nitrogen atoms.

Suitable alkylating agents are compounds comprising an alkyl group or alkyl derivative, having at least about four, preferably about six, carbon atoms, which is bonded to a leaving group such as a halo (e.g., chloro, bromo or iodo), tosylate, mesylate or epoxy group.

Examples of suitable alkylating agents which provide a hydrophobic group include alkyl halides (e.g., chlorides, bromides or iodides) such as n-hexyl halide, n-heptyl halide, n-octyl halide, n-nonyl halide, n-decyl halide, n-undecyl halide, n-dodecyl halide, n-tetradecyl halide, n-octadecyl halide, and combinations thereof. Other examples include: a dihaloalkane (e.g., a 1,10-dihalodecane); a hydroxyalkyl halide (e.g., an 11-halo-l-undecanol); an aralkyl halide (e.g., a bebnzyl halide); an alkyl epoxy ammonium salt(e.g., glycidtylpropyl-trimethylammonium salts) and epoxyalkylamides (e.g., N-(2, 3-epoxypropyl) butyramide or N-(2,3-epoxypropyl) hexanamide). Preferred halogen components of the alkyl halides are bromine and chlorine. Particularly preferred alkylating agents which, when reacted with the copolymer composition, will result in an copolymer reaction product: that includes an amine with a hydrophobic substituent, include, for example 1-bromodecane and 1-chlorodecane.

Examples of suitable alkylating agents which can provide a quaternary ammonium-containing moiety have the general formula:

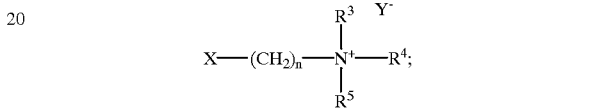

(XV)

wherein $R^3$, $R^4$, and $R^5$ represent an alkyl group, wherein each independently, is a normal or branched, substituted or unsubstituted alkyl group having about one to about twenty four carbon atoms, n is an integer, for example, n can have a value of three or more, X is a leaving group as described hereinabove, and Y is a negatively charged counterion.

When at least one of the three terminal substituents of the quaternary ammonium alkylating agent is a hydrophobic alkyl group having from about four to about twenty-four carbons, the alkylating agent therefore provides both a hydrophobic moiety and a quaternary ammonium-containing moiety. The alkylene group in this instance is three or more carbon atoms in length.

Particular examples of quaternary ammonium compounds suitable as alkylating agents include the following:
(4-bromobutyl)dioctylmethylammonium bromide;
(3-bromopropyl)dodecyldimesthylammonium bromide;
(3-chloropropyl)dodecyldimethylammonium bromide;
(3-chloropropyl)decyldimethylammonium bromide;
(5-tosylpentyl)dodecyldimfethylammonium bromide;
(6-bromohexyl)dimethyldecylammonium bromide
(12-bromododecyl)decyldimiethylammonium bromide;
(3-bromopropyl)tridecylammonium bromide;
(3-bromopropyl)docosyldimlethylammonium bromide;
(6-bromohexyl)docosyldimethylammonium bromide;
(4-chlorobutyl)dodecyldimethylammonium bromide;
(3-chloropropyl)octadecyldimethylammonium bromide;
(3-bromopropyl)octyldimethylammonium bromide;
(3-iodobutyl)dioctylmethylammonium bromide;
(2,3-epoxy propyl)decyldimethylammonium bromide; and
(3-bromohexyl)docosyldimethyammonium bromide Examples of suitable alkyl trimethylammonium alkylating agents include alkyl halide trimethylammonium salts, such as:
(4-halobutyl)trimethylammonium salt;
(5-halopentyl)trimethylammonium salt;
(6-halohexyl)trimethylammonium salt;
(7-haloheptyl)trimethylammonium salt;
(8-halooctyl)trimethylammonium salt;
(9-halononyl)trimethylammonium salt;

(10-halodecyl) trimethylarnmonium salt; (11-haloundecyl)trimethylammonium salt; (12-halododecyl)trimethylammonium salt; and combinations thereof. A particularly preferred quaternary ammonium- containing alkylating agent is (6-bromohexyl)-trimethylarnmonium bromide.

Alkylation of the amine-containing polymer or monomer can be achieved by reacting the polymer or monomer with an alkylating agent or combination of alkylating agents under conditions which are apparent to those of skill in the art. For example, the polymer composition can be combined with an alkylating agent in an aqueous caustic reaction solvent. The reaction mixture can be stirred at a temperature ranging from room temperature to about 75° C. The reaction period can typically be from about three to eighteen hours. The reaction product, an alkylated polymer composition, can then be recovered by filtration, washing and drying.

The amount of alkylating agent or agents used will depend on the specific polymer composition desired. For example, to produce a spirobicyclic ammonium moiety-containing copolymer composition comprising a hydrophobic substituent the total amount of alkylating agent combined with the copolymer is generally sufficient to result in reaction of the alkylating agent with about 10–100% of amine groups on the copolymer composition. For example, the alkylating agent can be present in an amount sufficient to cause reaction of the age:-t with about 50 to 100% or 75–100% of amine groups on the copolymer composition. As described above, amine-containing monomers can be alkylated prior to polymerization or amine-containing copolymers can be alkylated.

In a particular embodiment, the polymer comprises a N,N-diallylpiperazinium bromide monomer which can be prepared, for example, from mono-protected piperazine using standard amine-chemistry and the methods described herein. As used herein, the term "mono-protected piperazine" refers to a piperazine derivative wherein one of the amino nitrogen atoms is bonded to an amine-protecting group. Suitable amine-protecting groups include, for example, t-butoxycarbonyl (Boc), N-(9-fluorenylmethoxycarbonyl (Fmoc), benzyloxycarbonyl (Cbz), and the like. For example, N,N-diallylpiperazinium bromide can be prepared by reacting mono Boc-piperazine with allyl bromide as described herein. The product can then be deprotected by treatment with trifluoroacetic acid to expose a secondary amine, which can be substituted (e.g., alkylated) as described herein. Suitable substituents are as described herein and include, for example, a $C_1$–$C_{30}$ aliphatic group, $C_1$–$C_{30}$ alkyl group, a quaternary ammonium-containing group, a hydrophobic group and an aromatic group.

The spirobicyclic ammonium moiety-containing polymer can be linear or preferably crosslinked. Crosslinked polymer compositions comprise spriobicyclic ammonium moiety-containing copolymers which further comprise one or more additional monomers. For example, a multifunctional crosslinking co-monomer, as described above, can be incorporated into two or more growing polymer chains. Thus, the polymer composition can be crosslinked by polymerizing a monomer represented by structural formula (I) and/or (II) with a multifunctional crosslinking co-monomer as described above. Preferred multifunctional crosslinking co-monomers are 1,2-ethylene-bisacrylamide and 1,6-bis (diallylmethylammonium chloride)hexane.

In one embodiment, the multifunctional crosslinking co-monomer is an diallyl-, triallyl- or tetraallyl-derivative of piperazine, for example, N,N'-diallylpiperazine, N,N,N'-triallylpiperazinium bromide or other pharmaceutically acceptable salts of diallyl-, triallyl- or tetraallyl-d(erivatives of piperazine. Multifunctional crosslink:ing allyl-derivatives of piperazine can be prepared by reacting piperazine with a pharmaceutically acceptable allyl salt (e.g., allyl bromide) as described.

The amount of multifunctional crosslinking co-monomer is typically between 0.5 and 25 weight %, based upon the combined weight of said multifunctional co-monomer and spirobicyclic ammonium moiety-containing monomer. For example, the amount of multifunctional co-monomer can be 0.5–20%, or 1–10%.

The copolymers of the invention which comprise a spirobicyclic ammonium-moiety containing repeat unit and a nitrogen atom-containing repeat unit (e.g., an amine-containing monomer or an ammonium-containing monomer, as described herein) can be crosslinked by reacting the copolymer with one or more multifunctional crosslinking agents. The term "multifunctional crosslinking agent", as used herein, refers to a molecule having two or more reactive groups, such as electrophilic groups, which can react with amine (e.g., primary, secondary or tertiary amines) and/or ammonium groups to form a covalent bond. Crosslinking in this case can occur, for example, via nucleophilic attack of the polymer amine groups on the electrophilic groups. This results in the formation of a bridging unit which links two or more nitrogen atoms from different polymer strands. Multifunctional crosslinking agents of this type include compounds having two or more groups including, for example, acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes. A particularly preferred multifunctional crosslinking agent is epichlorohydrin.

Crosslinking of the copolymer can be achieved by reacting the copolymer with one or more multifunctional crosslinking agents in an aqueous caustic solution at about 25° C. for a period of time of about eighteen hours to thereby form a gel. The gel can then be combined with water and blended to form a particulate solid. The particulate solid can then be washed with water and dried under suitable conditions, such as a temperature of about 50° C. for a period of time of about eighteen hours.

Typically, the amount of multifunctional crosslinking agent that is reacted with the copolymer is sufficient to react with between about 0.5 and twenty percent of the nitrogen-containing co-monomers. For example, the amount of multifunctional crosslinking agent can be sufficient to react with about 5 to 15, or 2 to 6 percent of the nitrogen-containing co-monomers. It is to be understood that under certain conditions, hydroxyl groups contained in the polymer compositions can also react with the multifunctional crosslinking agent.

The copolymer can be crosslinked either prior to or subsequent to alkylation. In a particular example, the polymer composition is crosslinked prior to alkylation.

The polymers of the invention are non-toxic and stable when ingested by a mammal. By "non-toxic" it is meant that when ingested in therapeutically effective amounts neither the polymers themselves nor any ions released into the body upon ion exchange are harmful. By "stable" it is meant that when ingested in therapeutically effective amounts the polymer compositions do riot dissolve or otherwise decompose, in vivo, to form potentially harmful by- products, and remain substantially intact so that they can transport material out of the body.

The polymer of the invention are of sufficient size or are sufficiently crosslinked so as to prevent their absorption from the mammalian gastrointestinal tract. Thus, linear polymers of the invention are of a molecular weight greater than about 2,000 Daltons. Crosslinked polymers, however are not generally characterized by molecular weight. The crosslinked polymers discussed herein are, preferably, sufficiently crosslinked to resist absorption from the mammalian gastrointestinal tract.

The invention also provides methods of use of the spirobicyclic ammonium moiety-containing polymers of the invention. The method comprises the oral administration to a mammal of a therapeutically effective amount of a (e.g., one or more) spirobicyclic ammonium moiety-containing polymer to bind bile acids, reduce blood cholesterol, treat atherosclerosis, treat hypercholesterolemia and/or reduce plasma lipid content of the mammal. Generally, a therapeutic amount of a spirobicyclic ammonium moiety-containing polymer, is an amount in a range of from about 1 mg/kg/day to about 1 g/kg/day, preferably between about 1 mg/kg/day to about 200 mg/kg/day.

In one embodiment, the method of the invention is a method for binding bile acids in a mammal, comprising the step of orally administering to the mammal a therapeutically effective amount of a spirobicyclic ammonium moiety-containing polymer.

In another embodiment, the invention is a method for reducing blood cholesterol in a mammal, comprising the step of orally administering to the mammal a therapeutically effective amount of a spi:fobicyclic ammonium moiety-containing polymer. In still another embodiment, the invention includes a method for treating atherosclerosis in a mammal, comprising the step of orally administering to the mammal a therapeutically effective amount of a spirobicyclic ammonium moiety-containing polymer.

In still another embodiment, the method of the invention is that of treating hypercholesterolemia in a mammal, comprising the step of administering to the mammal a therapeutically effective amount of a spirobicyclic ammonium moiety-containing polymer.

The methods described herein can comprise the administration of a therapeutically effective amount of a polymer of the invention in combination with any known or later developed antihyperlipoproteinemic or cholesterol lowering agent or agents, for example, aryloxyalkanoic acid derivatives, HMG CoA reductase inhibitors, nicotinic acid derivatives, thyroid hormones and analogs and other bile acid sequestrants.

As used herein, the term, "therapeutically effective amount," refers to a quantity that is sufficient to bind bile acids, reduce blood cholesterol, treat atherosclerosis and/or treat hypercholesterolemia.

The spirobicyclic ammonium moiety-containing polymers of the invention include pharmaceutically acceptable salts of spirobicyclic ammonium moiety-containing polymers and copolymers. By the term, "salt", it is meant that the protonated spirobicyclic ammonium moiety and other protonated moieties or groups (e.g., substituents) on the polymer are associated wi-h an exchangeable negatively charged counterion. Examples of suitable counterions include $I^-$, $Cl^-$, $Br^-$, $CH_3SO_3^-$, $HSO_4^-$, $SO_4^{2-}$, $HCO_3^-$, $CO_3^-$, acetate, lactate, succinate, propionate, butyrate, ascorbate, citrate, maleate, folate, an amino acid derivative, or a nucleotide. The counterions can be the same as, or different from, each other. For example, the spirobicyclic ammonium moiety-containing polymer can contain two different types of counterions, both of which are exchanged for the bile acids being removed. More than one spirobicyclic ammonium moiety-containing polymer, each with different associated counterions, can be administered as well.

Alternatively, the spirobicyclic ammonium moiety-containing polymer can have the capability of becoming charged upon ingestion at physiological pH. In the latter case, the charged spirobicyclic ammonium ions and other protonated moieties or groups on the polymer also pick up negatively charged counterions upon ingestion that can be exchanged for bile acids.

The present invention further relates to spirobicyclic ammonium moiety-containing polymers as described herein for use in therapy (including prophylaxis) or diagnosis, and to the use of such spiro bicyclic moiety-containing polymers for the manufacture of a medicament for the treatment of a particular disease or condition as described herein (e.g., hypercholesterolemia, atherosclerosis).

The spirobicyclic ammonium moiety-containing polymer of the invention can be subsequently treated or combined with other materials to form compositions for oral administration of the spirobicyclic ammonium moiety-containing polymer.

The present pharmaceutical compositions are generally prepared by known procedures using well known and readily available ingredients. In making the spirobicyclic ammonium moiety-containing polymer of the present invention, the polymer and/or copolymer composition can be present alone, can by admixed with a carrier, diluted by a carrier, or enclosed within a carrier which can be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carriers, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, and talc.

While this invention has been particularly shown and described with references to preferred embodiments thereof, it will be understood by those skilled in the art that various changes in form and details may be made therein without departing from the spirit and scope of the invention as defined by the appended claims.

EXEMPLIFICATION

Example 1

Synthesis of N,N-diallylpyrrolidinium Bromide 177.8 9 of pyrrolidine dissolved in 280 mL of diethyl ether was added to a 1L 3—necked round-bottomed flask. The mixture was cooled to 5° C. with an ice bath. While stirring, 151 g of allyl bromide in 50 mL diethyl ether was added slowly to the pyrrolidine solution. After addition was complete, the reaction mixture was allowed to stir at room temperature for 18 hours. The white precipitate formed was filtered and ether was removed under reduced pressure. The residual liquid was fractionally distilled yielding 84 g of N-allylpyrrolidine. To a 500 mL, 3-neck round-bottomed flask was added 39 g of the N-allypyrrolidine dissolved in 40 mL of diethyl ether. After cooling to 5° C. with an ice bath, 42.5 g of allyl bromide in 40 mL of diethyl ether was added slowly. After completion of the addition of allyl bromide, the reaction mixture was allowed to warm to room temperature and stirred at room temperature for 24 hours. The solid residue thus formed was collected by filtration and was washed twice with 1.5 L of diethyl ether. The washed solid was dried under vacuum yielding 72 g of N,N-diallylpyrrolidinium bromide as a white solid.

Example 2
Synthesis of N,N-diallylpiperidinium Bromide 213 9 of piperidine dissolved in 300 mL of diethyl ether and was added to a 1 L 3-necked round-bottomed flask. The mixture was cooled to 5° C. with an ice bath. While stirring, a solution of 151.2 g of allyl bromide in 60 mL of diethyl ether was added slowly to the piperidine solution. After addition was complete, the reaction mixture was allowed to stir at room temperature for 18 hours. The white precipitate formed was removed by filtration. Ether was removed from the filtrate at room temperature using a rotary evaporator. The residual liquid was fractionally distilled yielding 108 g of N-allylpiperidine. To a 500 mL 3-necked round-bottomed flask was added 40.1 9 of N-allylpiperidine dissolved in 50 mL of diethyl either. After cooling to 5° C. with an ice bath, a solution of 38.7 g of allyl bromide in 30 mL of diethyl ether was added slowly. After completion of addition of allyl bromide the reaction mixture was allowed to warm to room temperature and stirred at room temperature for 24 hours. The solid residue thus formed was collected by filtration and was washed twice with 1.5 L of diethyl ether. The washed solid was dried under vacuum yielding 44 9 of N,N-diallylpiperidinium bromide as a white solid.

Example 3
Synthesis of N,N-diallylhomopiperidinium Bromide 198.4 9 of homopiperidine dissolved in 280 mL of diethyl ether was added to a 1 L, 3-necked round-bottomed flask. The mixture was cooled to 5° C. with an ice bath and while stirring, 121 g of allyl bromide in 40 mL of diethyl ether was added slowly to this amine solution. After addition was complete, the reaction mixture was allowed to stir at room temperature for 18 hours. The white precipitate thus formed was filtered and ether was removed at room temperature using a rotary evaporator. The residual liquid was fractionally distilled yielding 72 9 of N-allylhomopiperidine. To a 500 mL 3-necked round-bottomed flask was added 41.8 g of N-allylhomopiperidine dissolved in 50 mL of diethyl ether. After cooling to 5° C. with an ice bath, 36.3 g of allyl bromide in 30 mL diethyl ether was added slowly. After completion of the addition of allyl bromide, the reaction mixture was allowed to warm to room temperature and stirred at room temperature for 24 hours. The solid thus formed was collected by filtration and was washed twice with 1.5 L of diethyl ether. The washed solid was dried under vacuum yielding 67 g of N,N-diallyl-homopiperidinium bromide as a white solid.

Example 4
Synthesis of N,N-diallyl(4-hydroxy)piperidinium bromide.

To a 500 mL 3-necked round-bottomed flask, was added 24.0 g of 4-hydroxypiperidine dissolved in 140 mL of acetone. To this mixture was added 40.9 g of powdered anhydrous potassium carbonate. The reaction mixture was cooled to 5° C. with an ice bath. While stirring, 28.7 9 of allyl bromide in 60 mL acetone was added slowly to the reaction mixture. After addition was complete, the reaction mixture was allowed to stir at room temperature for 18 hours. The solid residue was removed by filtration, and acetone was removed from the filtrate using a rotary evaporator yielding 25.0 g of N-allyl(4-hydroxy)piperidine as viscous liquid. To a 500 mL 3-necked round-bottomed flask was added 20 g of N-allyl(4-hydroxy)piperidine dissolved in 75 mL diethyl ether. After cooling to 5° C. with an ice bath, 21.4 g of allyl bromide dissolved in 30 mL of diethyl ether was added slowly. After completion of addition of allyl bromide, the reaction mixture was allowed to warm to room temperature and stirred at room temperature for 24 hours. The solid residue thus formed was collected by filtration and was washed with diethyl ether (2×1.5 L). The washed solid was recrystallized from acetonitrile. After removal of acetonitrile by filtration, the residue was dried under vacuum yielding 22 9 of N,N-diallyl(4-hydroxy)piperidinium bromide as a white solid.

Example 5
Synthesis of N,N-diallyl 1,2,3,4-tetrahydroisoquinolinium Bromide.

To a 1L 3-necked round-bottomed flask, was added 100.0 g of 1,2,3,4-tetrahydroisoquinoline dissolved in 150 mL diethyl ether. The reaction mixture was cooled to 5° C. with an ice. While stirring, 45.4 g of allyl bromide in 60 mL diethyl ether was added slowly to the amine solution. After addition was complete, the reaction mixture was allowed to stir at room temperature for 18 hours. The reaction mixture was diluted with 300 mL diethyl ether, and the white precipitate was removed by filtration. Ether was removed from the filtrate under reduced pressure using a rotary evaporator yielding 64.0 g of N-allyl 1,2,3,4-tetrahydroisoquinoline as a viscous liquid. To a 500 mL 3-necked round-bottomed flask was added 61 g of N-allyl 1,2,3,4-tetrahydroisoquinoline dissolved in 100 mL diethyl ether. After cooling to 5° C. with an ice bath, 42.6 g of allyl bromide in 60 mL diethyl ether was added slowly. After completion of addition of allyl bromide, the reaction mixture was allowed to warm to room temperature and stirred at room temperature for 24 hours. The solid residue thus formed was collected by filtration and was washed with diethyl ether (2×500 mL). The washed solid was recrystallized from acetonitrile. After removal of acetonitrile by filtration, the residue was dried under vacuum yielding 55.0 g of N,N-diallyl 1,2,3,4-tetrahydroisoquinolinium bromide as a white solid.

Example 6
Synthesis of N,N-diallyldecahydroquinolinium Bromide.

To a 500 mL 3-necked round-bottomed flask, was added 24.0 g of decahydroquinoline dissolved in 150 mL acetone. To this mixture was added 29.7 g of powdered anhydrous potassium carbonate. The reaction mixture was cooled to 5° C. with an ice bath. While stirring, 20.8 g of allyl bromide in 50 mL acetone was added slowly to the reaction mixture. After addition was complete, the reaction mixture was allowed to stir at room temperature for 24 hours. The reaction mixture was filtered, and the solvent was removed from the filtrate under reduced pressure using a rotary evaporator yielding 23.0 g of N-allyl decahydroquinoline as a viscous liquid. To a 500 mL 3-necked round-bottomed flask was added 22.0 g of N-allyl decahydroquinoline dissolved in 100 mL diethyl ether. After cooling to 5° C. with an ice bath, 15.5 g of allyl bromide in 20 mL diethyl ether was added slowly. After completion of addition of allyl bromide, the reaction mixture was allowed to warm to room temperature and stirred at room temperature for 24 hours. The solid residue thus formed was collected by filtration and was washed with diethyl ether (2×500 mL). The washed solid was recrystalled from acetonitrile. After removal of acetonitrile by filtration, the residue was dried under vacuum yielding 24.0 g of N,N-diallyl decahydroquinolinium bromide as a white solid.

Example 7
Synthesis of Diallylammonium Chloride

To a 1 L 3-necked round-bottomed flask was added 202.8 9 of 37 wt % aqueous solution of hydrochloric acid. The flask containing the acid solution was cooled to 5° C. with an ice bath. While stirring, 200 g of diallylamine was added slowly to the acid solution. The temperature of the reaction mixture was kept below 30° C. during the addition process. After completion of addition, the reaction mixture was extracted with 300 mL of diethyl ether. The aqueous solution was bubbled with a slow stream of nitrogen for 2 hours to give 397.0 9 of an aqueous solution of diallylammonium chloride.

Example 8
Synthesis of N,N-Diallylpyrrolidinium Bromide-Diallylammonium Chloride Copolymer 23.22 9 of N,N-diallylpyrrolidinium bromide (EXAMPLE 1) and 3.34 g of diallylarnmonium chloride (EXAMPLE 7) were dissolved in 26.5 g of deionized water to make a 50% solution of the monomer. To the monomer solution was added 1.6 g of 2,2'-azobis(2-amindinopropane) dihydrochloride and the reaction mixture was bubbled with a slow stream of nitrogen gas for 45 minutes. While stirring the temperature was raised to 70° C. for 48 hours. After cooling to room temperature, 55 g of viscous polymer solution was obtained.

Example 9
Synthesis N,N-diallylpiperidinium Bromide-Diallylammonium Chloride Copolymer 24.62 g of N,N-diallylpiperidinium bromide (EXAMPLE 2) and 3.34 g of diallylammonium chloride (EXAMPLE 7) were dissolved in 28.0 g of deionized water to make a 50% solution of the monomer. To the monomer solution was added 1.7 g of 2,2'-azobis(2-amidinopropane) dihydrochloride and the reaction mixture was bubbled with a slow stream of nitrogen gas for 45 minutes. While stirring the temperature was raised to 70° C. and the reaction mixture was stirred at 70° C. for 48 hours. After cooling to room temperature, 58 g of viscous polymer solution was obtained.

Example 10
Synthesis of N,N-diallylhomopiperidinium Bromide-Diallylammonium Chloride Copolymer 26.0 g of N,N-diallylhomopiperidinium bromide (EXAMPLE 3) and 3.34 g of diallylammonium chloride (EXAMPLE 7) were dissolved in 29.0 g of deionized water to make a 50% solution of the monomer. To it was added 1.8 9 of 2,2'-azobis(2-amindinopropane) dihydrochloride and the reaction mixture was bubbled with a slow stream of nitrogen gas for 45 minutes. While stirring, the temperature was raised to 70° C. and the reaction mixture was stirred at 70° C. for 48 hours. After cooling to room temperature the polymer solution was diluted with 39 g of deionized water to make 30% polymer solution.

Example 11
Synthesis of N,N-diallyl(4-hydroxy)piperidinium Bromide-Diallylammonium Chloride copolymer.

N,N-diallylhomopiperidinium bromide (13.0 g, EXAMPLE 4) and diallylammonium chloride (2.7 g, EXAMPLE 7) were dissolved in 15.0 g deionized water. To this aqueous solution was added 0.5 g of 2,2'-azobis(2-amidinopropane) dihydrochloride, the reaction mixture was bubbled with a slow stream of nitrogen gas for 45 minutes. While stirring, the temperature was raised to 70° C. The reaction mixture was stirred at 70° C. for 48 hours. After cooling to room temperature, 30.0 g of viscous polymer solution was obtained.

Example 12
Synthesis of N,N-diallyl 1,2,3,4-tetrahydroisoquinolinium Bromide-Diallylammonium chloride copolymer.

N,N-diallyl 1,2,3,4-tetrahydroisoquinolinium bromide (15.0 g, EXAMPLE 5), and diallylammonium chloride (2.9 9, EXAMPLE 7) were dissolved in 18 mL deionized water. To this aqueous solution was added 0.5 g of 2,2'-azobis(2-amidinopropane) dihydrochloride, and the reaction mixture was bubbled with a slow stream of nitrogen gas for 45 minutes. While stirring, the temperature was raised to 70° C. The reaction mixture was stirred at 70° C. for 48 hours. After cooling to room temperature, 34.0 9 of viscous polymer solution was obtained.

Example 13
Synthesis of N,N-diallyldecahydroquinolinium Bromide-Diallyammonium Chloride Copolymer N,N-diallyldecahydroquinolinium bromide (8.0 g, EXAMPLE 6) and diallylammonium chloride (1.5 g, EXAMPLE 7) were dissolved in 10 mL deionized water. To this aqueous solution was added 0.3 g of 2,2'-azobis(2-amidinopropane)dihydrochloride, and the reaction mixture was bubbled with a slow stream of nitrogen gas for 45 minutes. While stirring, the temperature was raised to 70° C. The reaction mixture was stirred at 70° C. for 48 hours. After cooling to room temperature, 18.0 g of viscous polymer solution was obtained.

Example 14
Synthesis of Epichlorohydrin Crosslinked N,N-diallypyrrolidinium Bromide-Diallyammonium Chloride Copolymer 20 g of the 50% solution of N,N-diallylpyrrolidinium bromide-diallylammonium chloride copolymer (Example 8) was diluted with 10 mL of deionized water. While stirring, 0.38 g of 50% NaOH solution was added. When the temperature of the reaction dropped below 30° C., 0.37 mL of epichlorohydrin was added and stirring continued. After 18 hours, the reaction mixture gelled and the stirring was stopped. The polymer gel was left at room temperature for an additional 48 hours. The polymer was broken into smaller pieces and dispersed in 1 L of deionized water. After stirring for 40 minutes it was filtered. The filtered gel was suspended in 1 L of 2M NaCl solution, stirred for 30 minutes and filtered. After repeating the NaCl treatment four times, the filtered polymer was suspended in 1 liter of deionized water. The mixture was stirred for 30 minutes and filtered. This process was repeated. Subsequently, the polymer was suspended in 1 L of deionized water and 2 mL of concentrated HCl was added and the mixture was stirred for 30 minutes. The polymer was filtered and dried in a forced air oven at 60° C., yielding 6 g of the insoluble polymer as a pale white solid.

Example 15
Synthesis of Epichlorohydrin Crosslinked N,N-Diallylpiperidinium Bromide-Diallylammonium Chloride Copolymer 22 g of the 50% solution of N,N-diallylpiperidinium bromide-diallylammonium chloride copolymer (EXAMPLE 9) was diluted with 10 mL of deionized water. While stirring, 0.38 9 of 50% NaOH solution was added. When the temperature of the reaction dropped below 30° C., 0.35 mL of epichlorohydrin was added and stirring continued. After 18 hours, the reaction mixture gelled and the stirring was stopped. The polymer gel was left at room temperature for an additional 48 hours. The polymer was broken into smaller pieces and dispersed in 1 L of deionized water. After stirring for 40 minutes it was filtered. The filtered gel was suspended in 1 L of 2M NaCl solution, stirred for 30 minutes, and filtered. After repeating the NaCl treatment four times, the filtered polymer was suspended in 1 liter of deionized water. The mixture was stirred for 30 minutes and filtered. The polymer was resuspended in 1 L of deionized water and 2 mL of concentrated HCl was added and the mixture was stirred for 30 minutes. The polymer was filtered and dried in a forced air oven at 60° C., yielding 7.0 g of the insoluble polymer as an off-white solid.

Example 16
Synthesis of Epichlorohydrin Crosslinked N,N-diallylhomopiperidinium Bromide-Diallylammonium Chloride Copolymer To 33 g of the 30% solution of N,N-diallylhomopiperidin:ium bromide-diallylammonium chloride copolymer (EXAMPLE 10) was added 0.38 g of NaOH solution (50 wt % aqueous solution), and the reaction mixture was stirred. When the temperature of the medium dropped below 30° C., 0.33 mL of epichlorohydrin was added, and stirring continued until it gelled. The polymer gel was left at room temperature for an additional 72 hours. The polymer was broken into smaller pieces and dispersed in 1 L of deionized water. After stirring for 40 minutes, it was filtered. The filtered gel was suspended in 1 L of 2M NaCl solutions, stirred for 30 minutes, and filtered. After repeating the NaCl treatment three times, the filtered polymer was suspended in 1 L of deionized water. The mixture was stirred for 30 minutes and filtered. The process was repeated one more time. The polymer was resuspended in 1 L of deionized water, 2 mL of concentrated HCl was added, and the mixture was stirred for 30 minutes. The polymer was filtered and dried in a forced air oven at 60° C., yielding 7.0 g of the polymer as a pale white solid.

Example 17
Synthesis of Epichlorohydrin Crosslinked N,N-dially(4-hydroxy)piperidinium Chloride-Diallylammonium Chloride copolymer.

To 31 g of N,N-diallyl(4-hydroxy)pyridinium bromide-diallylammonium chloride copolymer solution (EXAMPLE 11) was added 21 mL of deionized water. While stirring, 0.25 g of 50% NaOH solution was added to this polymer solution. When the temperature of the reaction mixture dropped to below 30° C., 0.27 mL of epichlorohydrin was added, and stirring continued until it gelled. The polymer gel was left at room temperature for 72 hours. The polymer was broken into smaller pieces and dispersed in 1 L of deionized water. After stirring for 40 minutes, it was filtered. The filtered gel was suspended in 1 L of 2M NaCl solution, stirred for 30 minutes, and filtered. After repeating the NaCl treatment three more times, the filtered polymer was resuspended in 1 L of deionized water. The mixture was stirred for 30 minutes and filtered. This process was repeated one more time. The polymer was resuspended in 1 L deionized water, 2 mL of concentrated HCl was added, and the mixture was stirred for 30 minutes. The polymer was filtered and dried at 60° C., yielding 13.5 g of the polymer as an off-white solid.

Example 18
Synthesis of Epichlorohydrin Crosslinked N,N-diallyl 1,2,3,4-tetrahydroisoquinolinium Chloride-Diallylammonium chloride copolymer.

To 35.8 g of N,N-diailyl 1,2,3,4-tetrahydroisoquinolinium bromide-diallylammonium chloride copolymer solution (EXAMPLE 12) was added 10 mL of deionized water and 12 mL methanol. While stirring, 50% NaOH solution was added dropwise to this polymer solution to bring the pH>9.0. When the temperature of the reaction mixture dropped to below 30° C., 0.57 mL of epichlorohydrin was added. After stirring at room temperature for 10 hours, the temperature of the reaction mixture was raised to 60° C. The stirring continued at 60° C. until the solution gelled. The polymer gel was left at room temperature for 48 hours. The polymer was broken into smaller pieces and dispersed in 1 L of deionized water. After stirring for 40 minutes, it was filtered. The filtered gel was suspended in 1 L of 2M NaCl solution, stirred for 30 minutes, and filtered. After repeating the NaCl treatment three more times, the filtered polymer was suspended in 1 L of deionized water. The mixture was stirred for 30 minutes and filtered. This process was repeated one more time. The polymer was resuspended in 1 L deionized water, 5 mL of concentrated HCl was added, and the mixture was stirred for 30 minutes. The polymer was filtered and dried at 60° C., yielding 9.4 g of the polymer as an off-white solid.

Example 19
Synthesis of Epichlorohydrin Crosslinked N,N-Diallyldecahydroquinolinium Chloride-Diallylammonium Chloride Copolymer To 19 g of N,N-diallyldecahydroquinolinium bromide-diallylammonium chloride copolymer solution (EXAMPLE 13) was added 13 mL of deionized water. While stirring, 50% NaOH solution was added dropwise to this polymer solution to bring the pH>9.0. When the temperature of the reaction mixture dropped to below 30° C., 0.15 mL of epichlorohydrin was added. After stirring at room temperature for two hours, the temperature of the reaction mixture was raised to 60° C. Stirring was continued at 60° C. until the solution gelled. The polymer gel was left at room temperature for 72 hours. The polymer was broken into smaller pieces and dispersed in 1 L of deionized water. After stirring for 40 minutes, it was filtered. The filtered gel was suspended in 1 L of 2M NaCl solution, stirred for 30 minutes, and filtered. After repeating the NaCl treatment three more times, the filtered polymer was suspended in 1 L of deionized water. The mixture was stirred for 30 minutes and filtered. This process was repeated one more time. The polymer was resuspended in 1 L deionized water, 7 mL of concentrated HCl was added, and the mixture was stirred for 30 minutes. The polymer was filtered and dried at 60° C., yielding 5.7 g of the polymer as an off-white solid.

Example 20
Synthesis of Crosslinked Copolymer of N,N-Diallylpyrrolidinium Chloride and 1,2-ethylene- Bisacrylamide A solution of N,N-diallylpyrrolidinium bromide (10.0 g, Example 1), 1,2-ethylene-bisacrylamide (1.45 g) and 2,2'-azobis(2-amidinopropane)dihydrochloride) (0.1 g) in 10 mL of methanol, and 4 drops of deionized water was heated at 60° C. under an atmosphere of nitrogen for 12 hours. The resulting polymer gel was washed with methanol (3×500 mL). After filtration, the filtered gel was suspended in 500 mL of 2M NaCl solution, stirred for 30 minutes, and filtered. After repeating the NaCl treatment two more times, the filtered polymer was suspended in 1 L of deionized water. The mixture was stirred for 30 minutes and filtered. This process was repeated one more time. The polymer was resuspended in 1 L deionized water, 2 mL of concentrated HCl was added, and the mixture was stirred for 30 minutes. The polymer was filtered and dried at 60° C., yielding 6 g of the polymer as an off-white solid.

Example 21
Synthesis of Crosslinked Copolymer of N,N-Diallylpyrrolidinium Chloride and 1,6-bis (diallymethylammonium chloride)hexane A solution of N,N-diallylpyrrolidinium bromide (10.0 9, EXAMPLE 1), 1,6-bis(diallylmethylammcnium chloride) hexane (4 g) and 2,2'-azobiS(2-amidinopropane) dihydrochloride (0.1 g) in 10 mL of methanol and 4 drops of deionized water was heated at 60° C. under an atmosphere of nitrogen for 12 hours. The resulting polymer gel was washed with methanol (3×500 mL). After filtration, the filtered gel was suspended in 500 mL of 2M NaCl solution, stirred for 30 minutes, and filtered. After repeating the NaCl treatment two more times, the filtered polymer was suspended in 1 L of deionized water. The mixture was stirred for 30 minutes and filtered. This process was repeated one more time. Subsequently, the polymer was suspended in 1 L deionized water, 2 mL of concentrated HCl was added, and the mixture was stirred for 30 minutes. The polymer was filtered and dried at 60° C., yielding 7.1 g of the polymer as an off-white solid.

Example 22
Alkylation of Crosslinked Copolymers of N,N-diallylhomopiperidinium Chloride and Diallylammonium Chloride with 1-bromodecane Epichlorohydrin crosslinked copolymer of N,N-diallylhomopiperidinium chloride and diallylammonium chloride (5 g, EXAMPLE 16) was suspended in 200 mL of water:isopropanol mixture (1:1, v/v). The pH of this suspension was kept at >9.0, using 50% aqueous NaOH solution. While stirring, 5 g of 1-bromodecane was added to this suspension. After stirring at room temperature for 30 minutes, the temperature of the reaction mixture was raised to 75° C. After stirring at 75° C. for 18 hours, the reaction mixture was allowed to cool to room temperature. Concentrated HCl (2 mL) was added, and the mixture was stirred for 30 minutes. The polymer was filtered and was successively washed with 500 mL deionized water and 500 mL methanol. The polymer particles were suspended in 1 L of methanol and stirred for 30 minutes. After filtration, the polymer particles were suspended in 1 L of 2M NaCl solution, and the suspension was stirred for 40 minutes. The polymer was filtered, and this NaCl treatment was repeated one more time. After washing the filtered polymer with 1 L of deionized water, the polymer was suspended in 1 L of deionized water and stirred for 30 minutes. The filtered polymer was resuspended in 1 L of deionized water, and 5 mL of concentrated HCl was added. After stirring for 30 minutes, the polymer was filtered and was dried at 60° C., yielding 5.3 9 of an off-white solid.

In Vivo Testing

Example 23
Determination of Bile Acid Excreted

After a week of acclimation to our facility, the hamsters were transferred to special cages that separate urine and feces. They were given only water for a 24 hour period in order to synchronize their urge for food as a group. Following the 24 hour fast, they were presented a casein-based purified feed with 10% fat added plus a predetermined amount of the drug. The food was presented for a 72 hour period. Fecal material was collected for 63 hours, from the 9th to the 72nd hour. We were able to detect the point at which the animals began excreting the drug-containing diet due to the contrast in color (dark brown to white) in the two feeds. The fecal material was then freeze-dried to eliminate water weight from the material. It was then pulverized with an amalgamator to a uniform powder, and 1 9 was placed in the extraction cell. A solution of 80% methanol 100 mMol NaOH was used as the extraction solvent since :.t is a solvent most bile acids are sufficiently soluble in and is basic enough to hydrolyze bile acid esters. The esters commonly occur in the feces and become difficult to extract if not hydrolyzed. The extraction was accelerated by holding the sample and solvent at 100° C. and 1500 psi. 0.25 mL of the extract was evaporated and reconstituted in bovine calf serum. The sample was then analyzed like a standard serum sample, enzymatically, for bile and concentration. The concentration was multiplied by four times the volume of extract and expressed as the concentration per gram of feces. The results are presented in Table 1.

TABLE 1

In Vivo Bile Acid Sequestration Results of Crosslinked Spirobicyclic Ammonium Polymers

| Polymer Type | Dose (Wt % in Feed) | % Bile Acid Excreted Above Control |
| --- | --- | --- |
| EXAMPLE 8 | 0.2 | 140 |
| EXAMPLE 9 | 0.1 | 123 |
| EXAMPLE 10 | 0.2 | 405 |
| EXAMPLE 22 | 0.1 | 232 |
| EXAMPLE 11 | 0.1 | 135 |
| EXAMPLE 12 | 0.1 | 143 |
| EXAMPLE 13 | 0.1 | 296 |
| Colestipol | 0.3 | 110 |
| Cholestyramine | 0.3 | 125 |

What is claimed is:

1. A method for removing bile acids from a patient comprising administering to said patient a therapeutically effective amount of a spirobicyclic ammonium moiety-containing polymer, copolymer or salt thereof comprising a repeat unit having the structural formula:

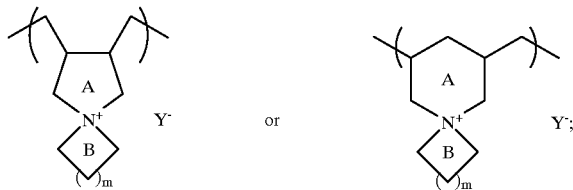

wherein
Y is a negatively-charged counter ion;
m is a integer from zero to about seven; and
Ring A and Ring B are each, independently, substituted or unsubstituted.

2. The method of claim 1 wherein the polymer is a homopolymer.

3. The method of claim 1 wherein the polymer is a copolymer further comprising one or more additional monomers.

4. The method of claim 3 wherein said additional monomer is a multifunctional co-monomer, said multifunctional co-monomer being present in an amount of about 0.5–25% by weight, based upon the combined weight of spirobicyclic ammonium moiety-containing monomer and multifunctional co-monomer.

5. The method of claim 3 wherein said additional monomer is a nitrogen-containing monomer.

6. The method of claim 5 wherein the spirobicyclic ammonium moiety-containing monomer is present in an amount of about 25–99% by weight, based upon the combined weight of spirobicyclic ammonium moiety-containing monomer and said nitrogen-containing monomer.

7. The method of claim 6 wherein the polymer is crosslinked by a multifunctional crosslinking agent, said agent being present in an amount of about 0.5–20% of nitrogen-containing monomers in the polymer.

8. The method of claim 7 wherein said multifunctional crosslinking agent is epichlorohydrin.

9. The method of claim 5 wherein said nitrogen-containing monomer is selected from the group consisting of allylamine, diallylamine, diallyl methylamine, vinylamine, acrylamide, meth acrylamide, aminoalkyl(meth)acry-lates and vinylimidazole.

10. The method of claim 5 wherein the nitrogen-containing monomer is an amine-containing monomer wherein the amino nitrogen atom is substituted by one or two substituents which can each, independently, be a hydrophobic group or a quaternary ammonium-containing group.

11. The method of claim 10 wherein said quaternary ammonium-containing group is:

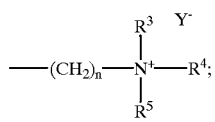

wherein, $R^3$, $R^4$ and $R^5$ are independently substituted or unsubstituted, normal or branched alkyl groups comprising about one to twenty-four carbon atoms;

n is an integer from one to about twenty; and

Y is a negatively-charged counter ion.

12. The method of claim 11 wherein:

$R^3$, $R^4$ and $R^5$ are methyl groups, and n is an integer from about three to twelve.

13. The method of claim 12 wherein at least one of $R^3$, $R^4$ and $R^5$ is a hydrophobic alkyl group having from four to about twenty-four carbon atoms, the remainder of which each, independently, have from one to twenty-four carbon atoms.

14. The method of claim 13 wherein at least two of $R^3$, $R^4$ and $R^5$ are hydrophobic alkyl groups having from four to about twenty-four carbon atoms, the remainder having from one to twenty-four carbon atoms.

15. The method of claim 13 wherein all three of $R^3$, $R^4$ and $R^5$ are hydrophobic alkyl groups having from four to about twenty-four carbon atoms.

16. The method of claim 10 wherein said hydrophobic group is a substituted or unsubstituted, normal, branched or cyclic alkyl group comprising four to about thirty carbon atoms.

17. The method of claim 16 wherein said hydrophobic group comprises four to about fourteen carbon atoms.

18. The method of claim 5 wherein said additional monomer is an ammonium-containing monomer.

19. The method of claim 18 wherein said ammonium-containing monomer is:

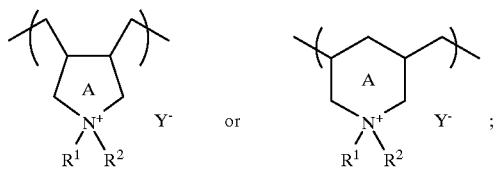

or a combination thereof; wherein

Y is a negatively-charged counter ion; and $R^1$ and $R^2$ can each, independently, be hydrogen, a $C_1$–$C_{30}$ aliphatic group, $C_1$–$C_{30}$ alkyl group, a quaternary ammonium-containing group or an aromatic group.

20. The method of claim 19 wherein $R^1$ and $R^2$ are each independently hydrogen or a $C_1$–$C_{12}$ alkyl group.

21. A method for removing bile acids from a patient, comprising administering to said patient a therapeutically effective amount of a spirobicyclic ammonium moiety-containing polymer, copolymer or salt thereof comprising a repeat unit having the structural formula:

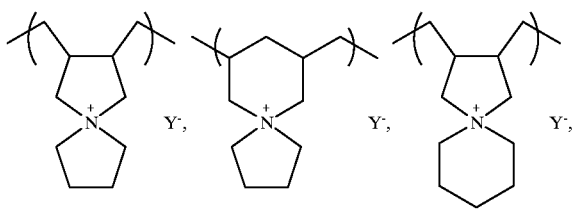

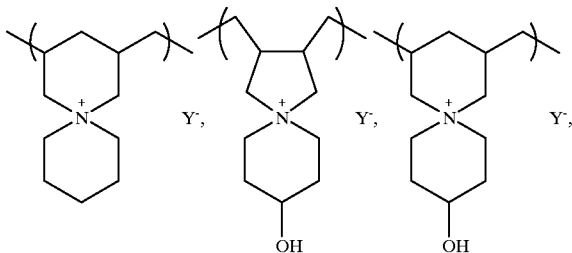

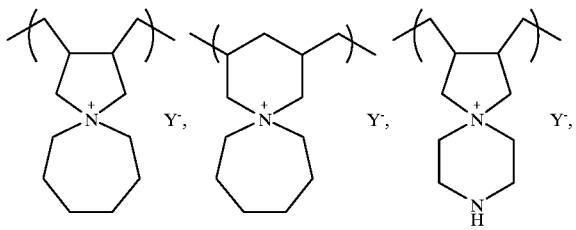

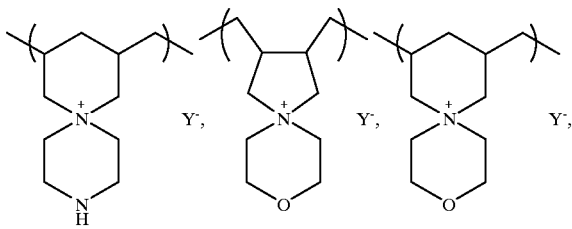

-continued

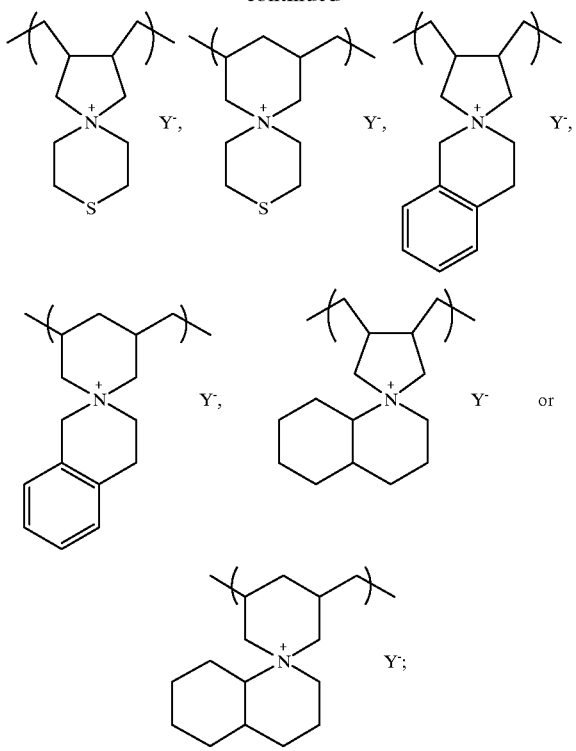

wherein Y is a negatively-charged counter ion.

22. A method for removing bile acids from a patient, comprising administering to said patient a therapeutically effective amount of a spirobicyclic ammonium moiety-containing polymer, copolymer or salt thereof comprising a repeat unit having the structural formula:

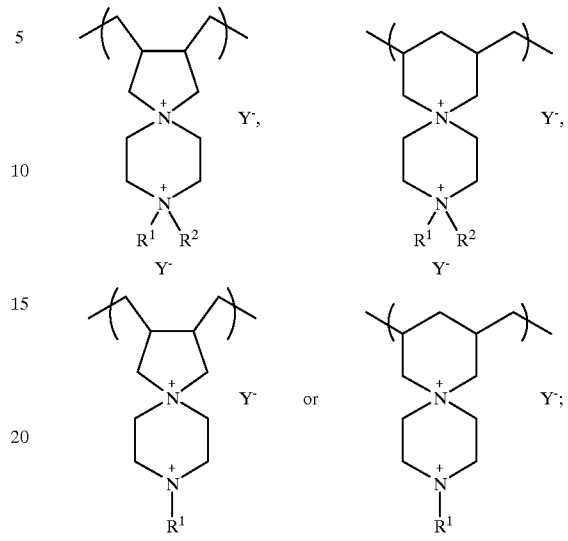

wherein $R^1$ and $R^2$ can each independently be hydrogen, a $C_1$–$C_{30}$ aliphatic group, $C_1$–$C_{30}$ alkyl group, an aromatic group, a quaternary ammonium-containing group or a hydrophobic group, and Y is a negatively-charged counter ion.

* * * * *